US005567436A

United States Patent [19]

Udelle

[11] Patent Number: 5,567,436

[45] Date of Patent: Oct. 22, 1996

[54] PROCESS FOR LIQUID CATNIP AROMAS

[76] Inventor: Steven D. Udelle, 26414 Barranquilla Ave., Punta Gorda, Fla. 33983

[21] Appl. No.: 396,455

[22] Filed: Feb. 28, 1995

Related U.S. Application Data

[63] Continuation-in-part of Ser. No. 217,931, Mar. 25, 1994, abandoned.

[51] Int. Cl.$^{6}$ .................................................. A61K 35/78

[52] U.S. Cl. ......................... 424/439; 424/45; 424/195.1; 424/484

[58] Field of Search .................................... 424/195.1, 45, 424/484

[56] References Cited

U.S. PATENT DOCUMENTS

| | | | |
|---|---|---|---|
| 2,005,817 | 6/1935 | Yoder | 119/29.5 |
| 4,771,732 | 9/1988 | Carney | 119/29 |
| 4,880,627 | 11/1989 | Trenzeluk | 424/640 |
| 4,928,632 | 5/1990 | Gordon | 119/29.5 |
| 5,009,193 | 4/1991 | Gordon | 119/29.5 |
| 5,275,127 | 1/1994 | Leopold | 119/706 |

FOREIGN PATENT DOCUMENTS

| | | | |
|---|---|---|---|
| WO9104657 | 4/1991 | WIPO | A01K 29/00 |

*Primary Examiner*—Thurman K. Page
*Assistant Examiner*—Sharon Howard

[57] ABSTRACT

Aromatic oils and flavor from the herbaceous plant catnip are extracted through absorption, or infusion, by a liquid, wherein the aroma laden liquid is misted to animal device surfaces for enticement purposes.

10 Claims, No Drawings

PROCESS FOR LIQUID CATNIP AROMAS

THIS APPLICATION IS A CONTINUATION-IN-PART OF APPLICATION SER.NO. 08/217,931 FILED 03/25/94, NOW ABANDONED.

FIELD OF THE INVENTION

The present invention deals with herbaceous plant material, and more particularly to a method or process of extracting by absorption or infusion to a liquid, the aromatic oil and flavor inherent to a plant, whereby the aroma laden liquid concept is used as a misting enticement through light application to self grooming devices and exercise and amusement toys used by domesticated animals.

BACKGROUND OF THE PRIOR ART

Certain herbaceous plant species contain aromatic oils and flavor within their flowers, leaves, and stems that are irresistible to cats. One species called Catnip, (Nepeta cataria L.) has a defense mechanism that secretes its oil to ward off insects that otherwise would eat its leaves. This defense mechanism goes awry when cats discover this plant. In their ecstatic rolling, and rubbing against the plant, they may destroy it entirely, for they quickly learn that the more they demolish the plant, the more pleasurable oil is released. Cats are known to get a euphoric high on catnip. Catnip has minor medicinal value, as most of its medicinal claims have been erroneous. Catnip is a species belonging to the mint family (Labiatae). Catnip is considered a common weed in North America, Europe, and Asia. Catnip is known also as catment, catmint, and cats-toy. Other Labiatae family members are mint, spearmint, peppermint, and lemon scented citradora. These Labiatae varieties are scientifically labeled Nepeta Cataria which always precedes their individual names. Further descriptions and writings are referenced in books at the library, including Magic and Medicine of Plants (Readers Digest Assoc.), Wild Flowers of the United States (New York Botanical Gardens), Macmillan Treasury of Herbs (Macmillan Press), Encyclopedia of Gardening (Greystone Press), Wild Flowers of Eastern America (Alfred E. Knopf), Flower Finder (American Horticultural Society), Health Plants of the World (Newsweek Books). Animal devices that utilize catnip as an incentive are U.S. Pat. No. 2,005,817, by Yoder, Jun. 25, 1935, showing a vertical scratching post accommodating a dry catnip incentive recess within the post body covered by a claw scratching carpet. U.S. Pat. No. 4,771,732, by Carney, Sep. 20, 1988, shows an animal amusement flexible bag having a dry animal attractant applied thereto. U.S. Pat. No. 4,928,632, by Gordon, May 29, 1990 shows an animal toy comprising a flexible plastic tube having a dry material such as catnip within its interior, having a plurality of pores which open when an animal chews upon the tube, thus releasing a catnip aroma. U.S. Pat. No. 5,009,193, by Gordon, Apr. 23, 1991, shows a closed circuit track containing a hollow ball having small holes for releasing aromas from dry catnip within the shell of the ball. U.S. Pat. No. 5,275,127 by Leopold, Jan. 4, 1994, shows a rotatable cylindrical claw scratching device, wherein the base of the device also includes a tray containing dry catnip. U.S. Pat. No. WO 91/04657, by Koho, Apr. 18, 1991, shows a cat attractant applicator in the shape of a penholder. The object is to apply a liquid attractant from a brush or pen nib onto a surface, to entice an animal to the applied surface. This device is expensive to make, time consuming to apply, and would be difficult to apply to grooming brush bristles.

SUMMARY OF THE INVENTION

Catnip is widely available in a dried, broken form only, and is sold in small packaged quantities usually in ½ ounce portions for use as an incentive, or enticement for domesticated cats. The primary use of catnip is to promote more frequent use or attention to self grooming devices and toys used for exercise or amusement by a cat, thereby maintaining or improving the animal's well being through its own initiative. Catnip in its widely used form is wasted, as many devices do not have a recess or compartment for its placement. As a result, when dispersing the dry material on or around these devices, unnecessary waste and untidiness occurs. The intended use of these devices may be considerably limited, because of the absence of accommodation for the catnip material. Catnip in its dry state, when placed in recesses and compartments, quickly loses its aromatic value, as the oil evaporates to the surrounding air causing further waste as more catnip must be provided. Generally, the present invention deals with a method or process of extracting, or transferring aromatic oil laden herbaceous plant material or substances by infusion, or absorption of these particles by potable water, whereby the water soluble aromatic oils inherent within the substance pieces or bits, may be released by absorption or infusion to the water or liquid. The extraction by absorption of the herbaceous aromatic laden oils to the liquid can be accomplished by using ordinary tap water temperatures, or by boiling. This method or process of aroma and taste absorption by a liquid is readily recognized by the act of brewing coffee, tea, or iced tea made without the need of hot, or boiled water.

It is therefore an object of the present invention to simplify the application of catnip incentive or enticements through the concept of administering with ease and convenience, measured amounts of light misting of aroma laden liquid to animal self grooming devices, and toys used for exercise and amusement, by means of a finger spray pump or aerosol can.

Another object of the invention is to capture and contain by absorption or infusion, the maximum amount present in fresh herbaceous material, or aromatic laden oil that otherwise would be lost when used in the currently dry particle form.

Still another object of the invention is the containment of the aroma laden liquid in a closed bottle-like spray receptacle which will insure long term freshness and potency of its contents, and be ready for use with a simple push of a finger.

Another object of the invention is to provide a much greater productive volume of herbaceous aroma laden liquid from substantially smaller amounts of concentrated base aroma laden material or substance, thereby reducing waste and cost significantly.

Yet another object of the invention is that portions of the aroma laden liquid can be served as a drink fortified with vitamins and given to an animal.

Another object of the invention is that the herbaceous pulp can be made into wafer treats when combined with an edible organic binder.

Other advantages of the present invention will be readily understood by reference to the following detailed description.

DETAILED DESCRIPTION OF THE INVENTION

1. The first method or process of extracting the aromatic oils and flavor from herbaceous material or substances through infusion or absorption by a liquid is as follows, 1 ounce of fresh or top grade dried, Nepeta cataria L. or catnip, 192 ounces (6 qts.) of potable water, Place the above in a suitable sized cooking-vessel with a heavy, proper fitting lid, Heat and bring contents to a boil for about 15 seconds, Let cool without removing lid, When cool, pour the liquid and pulp material into a container and seal with a cap or tight lid if solution is to be stored as surplus inventory.

This short term storage is desirable, as the water can absorb any further aromatic oil given off by the herbaceous pulp material. The solution will also be ready for immediate bottling upon cooling if needed. The solution should be filtered for pulp separation prior to being pumped to the bottling line. The herbaceous pulp can be retrieved and made into dry animal wafer treats using an edible organic binder means, thereby utilizing the benefits of the herbaceous substances completely.

2. The second and preferred method or process of extracting the aromatic oils and flavor from herbaceous materials through absorption by a liquid is as follows, 1 ounce of fresh or top grade dried, Nepeta cataria L. or catnip, 25 ounces of potable water at its present tap temperature, Place both in a blender with a tight fitting cover, Operate blender at high speed for about a minute to reduce the herbaceous material into smaller bits, Pour contents into storage container and add a sufficient amount of preservative, Add 167 ounces of additional tap water, (6 qts. total), briefly stir, then seal storage container with a cap or lid.

The solution can remain in inventory, or be bottled immediately after filtering the pulp, including making the pulp into wafer treats. This preferred method or process will not require expensive fuel for heating the water, as the temperature is more than satisfactory right from the tap, at whatever temperature it may be at the time. The purpose of adding a portion of water to the 1 ounce of herbaceous material was to provide a vehicle for the substance in the blending breakdown process. The water vehicle will provide a more uniform substance reduction and contain any possible loss of aroma given off by the substance as they are rendered. The smaller bits serve to hasten aroma and taste absorption when used with colder liquids. Blending or crushing the substance dry without a liquid vehicle causes substantial loss of aroma to the surrounding air and does not provide uniform rendering. The chlorinated tap water has had no adverse effect on the performance of the solution. The color of the first and second batches of solution seem identical after 8 months exhibiting a light brown color with a greenish cast. The aroma note on both test batches seem the same, and the taste of each are similar, and they were not refrigerated at any time. Both test batches work equally well when used on devices at the time of this writing. It should be noted that since catnip is grown in many areas of the country, where temperatures, nutrients, and soil conditions differ, the catnip plant (Nepeta cataria L.) will not consistently present the same high level of aromatic potency desired. These variables of aromatic potency from some catnip plants may only yield less than one quart of useful extract solution when using one ounce of dry catnip particles in the absorption process. The volume of water for absorption of aromas from one ounce of dried catnip material will have to be predetermined by the initial quality and freshness of the dry catnip material beforehand. The thicker branches or stems of the plant may be used, thereby utilizing more of the plant oil for extraction in a smaller ratio of 10 to 1. The finished product derived from these first and second methods were placed in closed storage containers. The amount of solution needed for testing was 1 quart removed from each storage container, and placed in 1 quart trigger spray bottles. One bottle was labeled "hot" and the second bottle was labeled "cold." The samples were tested over a period of 6 months on a group of self grooming devices and various toys used by two mature cats, ages 9, and 13 years. The devices were sanitized and placed short distances from each other. One device was selected for misting by alternating the test samples of the catnip aroma solution. The two cats would easily find this device and spend some time rubbing it, or playing with it. Any tested device was washed and sanitized, prior to spraying an alternate device. A schedule of spraying an alternate device every fifth day revealed that one or both cats would frequent that device longer than the other sanitized aroma free devices. Since the misting spray lacks solid particles, and only dispenses aromatic liquid to scratching pads, grooming brushes, and toy surfaces, the aromas dissipate in several days. However, since the aromatic spray solution has a stronger aromatic note when sprayed directly to the device surfaces than dry catnip stored in a compartment, more activity takes place from the animal. Since the sanitized device is misted every five days, and the gradual dissipation of the misted aromas on the device surfaces are of several days duration, the remaining three days serve as a break from the enticement aromas, and the cat in the meantime, becomes more adept at using the device without the need for constant enticement. It would be wrong to provide a device with a concentrated aroma continuously as this is not good for the animal or the intended purpose of the device. It should be used as a scheduled treat for the animal as well as a device enticement. Too much of a good thing can defeat the intended objectives. A once a week schedule of misting animal devices would also be appropriate. Animal grooming devices and toys should be washed and sanitized regularly to remove animal dirt and body oil, which can accumulate and cause unwanted odors. A clean device is more effective when misting with the aromatic solution. After 8 months of regular use, there is a balance of about two thirds quart of solution remaining in each of the originally filled spray bottles.

CONCLUSION

Although the description above contains many specificities, the concepts outlined should not be construed as limiting the scope of the invention, but as merely providing ways, means, or methods in performing or initiating the presently preferred examples or concepts of this invention. For example, it would be obvious to use herbaceous materials that were fresh cut and not dried for infusion or absorption. The ratio of water to lower grade quality herbaceous material would be substantially less, than with fresh material. Other herbaceous substances or material such as spearmint, peppermint, and Nepeta Cataria 'Citradora' can be infused or absorbed by larger ratios of water, to reduce their pungent aroma notes, to work well as an enticement. Tarragon, from the Artemesia group requires a greater ratio of water to subdue its overwhelming aroma note, to be useful as an enticement to cats. The misting concept opens up an area where herbaceous materials from other unrelated species may have enticement value. It would also be obvious to substitute natural, herbaceous aromatic oils with an artificial or synthetic means that may duplicate animal enticement aromas to be put into liquid form by infusion or absorption or just by mixing, for misting animal self grooming and exercise and amusement toys. The above specifications should clearly define the effectiveness of the aroma laden misting concept, its utility, ease of application, and economy.

I claim:

1. A method or process for extracting aromatic oil and flavor from certain selected herbaceous plants by absorption to a liquid comprising:

(a) 1 ounce of fresh or high grade dried Nepeta cataria particles, (b) 192 ounces, or 6 quarts of potable, unheated tap water, (c) store said Nepeta cataria particles, and said potable unheated tap water mixture in a sealed container, (d) filter said Nepeta cataria particle pulp from extract solution prior to filling finger pump spray applicator bottle used for misting animal devices, (e) filling said finger pump spray applicator bottle with a sealed containment of the aroma laden liquid.

2. A method or process of claim 1, wherein a sufficient amount of preservative is added to said extract solution, if long-term inventory is contemplated.

3. A method or process of claim 1, wherein said Nepeta cataria particles may be boiled for a predetermined period of time in said potable unheated tap water for extraction/of said aromatic oil and flavor.

4. A method or process of claim 1, wherein said 192 ounces of potable unheated tap water can be reduced to 10 ounces when an ounce of said Nepeta cataria particles are of a particularly low grade, due to an overabundance of small branch stem particles, thereby extracting a useful solution ratio of 10 to 1, and therefore utilizing more of the plant.

5. A method or process of claim 4, wherein said useful solution ratio is predetermined by the initial quality, freshness, and parts of the Nepeta cataria plant material beforehand.

6. A method or process of claim 1, wherein said extract solution originates from a period of soaking by said Nepeta cataria particles in said potable unheated tap water.

7. A method or process of claim 1, wherein said potable unheated tap water mixture provides a substantially greater productive volume of said aromatic oil from a much smaller amount of concentrated aroma laden material.

8. A method or process of claim 1, wherein said extract solution in said finger pump spray applicator bottle used for lightly misting animal devices, provides an efficient and economical concept of use for animal enticements and application.

9. A method or process of claim 1, wherein said Nepeta cataria particle pulp is retrieved and partially mixed with an edible organic binder, thereby producing dry wafer treats for said animal.

10. A method or process of claim 1, wherein said extract solution is fortified with vitamins and serves as an occasional drink to an animal.

* * * * *